(12) United States Patent
Shao et al.

(10) Patent No.: US 7,517,664 B2
(45) Date of Patent: Apr. 14, 2009

(54) INACTIVATED ENZYME VARIANTS AND ASSOCIATED PROCESS AND REAGENT SYSTEM

(75) Inventors: Zhixin Shao, Penzberg (DE); Joachim Hoenes, Zwingenberg (DE); Carina Horn, Biblis (DE); Wolfgang-Reinhold Knappe, Ludwigshafen (DE); Rainer Schmuck, Benediktbeuern (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/559,607

(22) Filed: Nov. 14, 2006

(65) Prior Publication Data

US 2007/0087398 A1 Apr. 19, 2007

Related U.S. Application Data

(62) Division of application No. 10/975,697, filed on Oct. 28, 2004, now Pat. No. 7,172,890.

(51) Int. Cl.
*C12Q 1/32* (2006.01)
*C12Q 1/54* (2006.01)
*C12N 9/04* (2006.01)
*C12N 1/20* (2006.01)

(52) U.S. Cl. .............................. 435/14; 435/26; 435/190
(58) Field of Classification Search ........................ None
See application file for complete search history.

(56) References Cited

U.S. PATENT DOCUMENTS 4,238,565 A 12/1980 Hornby et al.

FOREIGN PATENT DOCUMENTS

| EP | 1382683 | 1/2004 |
|---|---|---|
| GB | 2188728 | 10/1987 |

OTHER PUBLICATIONS

Ofran, et al.Durg discov. Today. 2005, 10, pp. 1475-1482.*
Nagao et al., "Cloning, nucleotide sequences, and enzymatic properties of glucose dehydrogenase isozymes from *Bacillus megaterium* IAM1030", *Journal Bacteriology*, vol. 174, 1992, pp. 5013-5020.
Mitamura et al., "Enzymatic properties of isozymes and variants of glucose dehydrogenase from *Bacillus megaterium*", *European Journal of Biochemistry*, vol. 186, 1989, pp. 389-393.
Heilmann et al., "Identification and isolation of glucose dehydrogenase genes of *Bacillus megaterium* M1286 and their expression in *Escherichia coli*", *European Journal of Biochemistry*, vol. 174, 1988, pp. 485-490.
Makino et al., "Stability-increasing mutants of glucose dehydrogenase from *Bacillus megaterium* IWG3"*Journal of Biological Chemistry*, vol. 264, 1989, pp. 6381-6385.
Ramaley et al., "Glycerol protection and purification of *Bacillus subtilis* glucose dehydrogenase", *Journal of Biological Chemistry*, vol. 258, 1983, pp. 12558-12565.
Pauly et al., "D-glucose dehydrogenase from *Bacillus megaterium* M 1286: purification, properties and structure", *Hoppe Seylers Z Physiol Chem.*, vol. 356, 1975, pp. 1613-1623.
Shao et al., "Engineering new functions and altering existing functions", *Curr. Opin. Struct. Biol.*, vol. 6, No. 4, 1996, pp. 513-518.
Schlereth et al., "Self-assembled monolayers with biospecific affinity for NAD(H)-dependent dehydrogenases: characterization by surface plasmon resonance combined with electrochemistry 'in situ'", *Journal of Electroanalytical Chemistry*, vol. 444, 1998, pp. 231-240.
Cozier et al., "Characterization of the membrane quinoprotein glucose dehydrogenase from *Escherichia coli* and characterization of a site-directed mutant in which histidine-262 has been changed to tyrosine", *Biochemical Journal*, vol. 340, 1999, pp. 639-647.
Slama et al., "Carbanicotinamide adenine dinucleotide: synthesis and enzymological properties of a carbocyclic analog of oxidized nicotinamide adenine dinucleotide", *Biochemistry*, vol. 27, No. 1, 1988, pp. 183-193.
Cadwell et al., "Mutagenic PCR", *PCR Methods Appl.*, vol. 3, No. 6, 1994, pp. 136-140.
Bach et al., "Aerobic sporulation bacteria. I. Glucose dehydrogenase of *Bacillus cereus*", *Journal Bacteriology*, vol. 83, 1962, pp. 699-707.
Mitamura et al., "Structure of isozyme genes of glucose dehydrogenase from *Bacillus megaterium* IAM1030", *Journal of Ferment. Bioeng.* vol. 70, 1990, pp. 363-369.
Makino et al., "Purification and characterization of mew glucose dehydrogenase from vegetative cells of *Bacillus megaterium*" *Journal of Ferment. Bioeng.*, vol. 67, 1989, pp. 372-379.
Lampel et al., "Characterization of the deveopmentally regulated *Bacillus subtilis* glucose dehydrogenase gene", *Journal of Bacteriology*, vol. 166, 1986, pp. 238-243.

* cited by examiner

*Primary Examiner*—Nashaat T Nashed
*Assistant Examiner*—MD. Younus Meah
(74) *Attorney, Agent, or Firm*—Barnes & Thornburg LLP

(57) ABSTRACT

The present invention relates to oxidoreductase apoenzyme variants which are enzymatically inactive but have coenzyme-binding properties. Further, the present invention relates to DNA sequences encoding these oxidoreductase apoenzyme variants, expression vectors containing such DNA sequences and the use of these oxidoreductase apoenzyme variants in diagnostic applications.

12 Claims, 15 Drawing Sheets

Bs GlucDH DNA sequence    (SEQ ID NO: 05)

ATGTATCCGGACTTAAAAGGAAAAGTCGTCGCTATTACAGGAGCTGCTTCAGGGCTCGGAAAGGCAATG
GCCATTCGCTT
CGGCAAGGAGCAGGCAAAAGTGGTTATCAACTATTATAGTAATAAACAAGATCCGAACGAGGTAAAAGA
AGAGGTCATCA
AGGCGGGCGGTGAAGCTGTTGTCGTCCAAGGAGATGTCACGAAAGAGGAAGATGTAAAAAATATCGTG
CAAACGGCAATT
AAAGAGTTCGGCACACTCGATATTATGATTAATAATGCCGGTCTTGAAAATCCTGTGCCATCTCACGAAA
TGCCGCTTAA
GGATTGGGATAAAGTCATCGGCACAAACTTAACAGGTGCCTTTTTAGGAAGCCGTGAAGCGATTAAATA
TTTCGTAGAAA
ACGATATCAAGGGAAATGTCATCAACATGTCCAGTGTGCACGAAGTGATTCCTTGGCCGTTATTTGTTCA
CTACGCGGCA
AGTAAAGGCGGGATAAAGCTGATGACAGAAACATTGGCGTTGGAATACGCGCCGAAGGGCATTCGCGT
GAACAATATCGG
GCCAGGTGCGATCAATACGCCAATCAATGCTGAAAAATTTGCTGACCCTAAACAGAAAGCAGATGTAGA
AAGCATGATTC
CGATGGGGTATATCGGCGAACCGGAGGAGATCGCCGCAGTGGCAGTGTGGCTTGCTTCGAAGGAATC
CAGCTATGTTACA
GGCATCACATTGTTTGCGGACGGCGGAATGACGAAATATCCTTCTTTCCAGGCAGGCCGCGGTTAA

Fig. 2

BsGlucDH protein sequence (SEQ ID NO. 06)

MYPDLKGKVVAITGAASGLGKAMAIRFGKEQAKVVINYYSNKQDPNEVKEEVIKAGGEAVVVQGDVTKEEDV
KNIVQTAI
KEFGTLDIMINNAGLENPVPSHEMPLKDWDKVIGTNLTGAFLGSREAIKYFVENDIKGNVINMSSVHEVIPWPL
FVHYAA
SKGGIKLMTETLALEYAPKGIRVNNIGPGAINTPINAEKFADPKQKADVESMIPMGYIGEPEEIAAVAVWLASK
ESSYVT
GITLFADGGMTKYPSFQAGRG

Fig. 3

RC21 DNA sequence    (SEQ ID NO: 07)

ATGTATCCGGACTTAAAAGGAAAAGTCGTCGCTATTACAGGAGCTGCTTCAGGGCTCGGAAAGGCAATGGCCATTCGCTT

CGGCAAGGAGCAGGCAAAAGTGGTTATCAACTATTATAGTAATAAACAAGATCCGAACGAGGTAAAAGAAGAGGTCATCA

AGGCGGGCGGTGAAGCTGTTGTCGTCCAAGGAGATGTCACGAAAGAGGAAGATGTAAAAAATATCGTGCAAACGGCAATT

AAAGAGTTCGGCACACTCGATATTATGATTAATAATGCCGGTCTTGAAAATCCTGTGCCATCTCACGAAATGCCGCTTAA

GGATTGGGATAAAGTCATCGGCACAAACTTAACAGGTGCCTTTTTAGGAAGCCGTGAAGCGATTAAATATTTCGTAGAAA

ACGATATCAAGGGAAATGTCATCAACATGTCCACCGTGCACGAAGTGATTCCTTGGCCGTTATTTGTTCACTACGCGGCA

AGTAAAGGCGGGATAAAGCTGATGACAGAAACATTGGCGTTGGAATACGCGCCGAAGGGCATTCGCGTGAACAATATCGG

GCCAGGTGCGATCAATACGCCAATCAATGCTGAAAAATTTGCTGACCCTAAACAGAAAGCAGATGTAGAAAGCATGATTC

CGATGGGGTATATCGGCGAACCGGAGGAGATCGCCGCAGTGGCAGTGTGGCTTGCTTCGAAGGAATCCAGCTATGTTACA

GGCATCACATTGTTTGCGGACGGCGGAATGACGAAATATCCTTCTTTCCAGGCAGGCCGCGGTTAAAAGCTTGGCTGTTT

TGGCGGATGAGAGAAGATTTTCAGCCTGATACAGATTAAATCAGAACGCAGAAGCGGTCTGATAAAACAGAATTTGCCTG

GCGGCAGTAGCGCGGTGGTCCCACCTGACCCCATGCCGAACTCAGAAGTGAAACGCCGTAGCGCCGATGGTAGTGTGGGG

TCTCCCCATGCGAGAGTAGGGAACTGCCAGGCATCAAATAAAACGAAAGGCTCAGTCGAAAGACTGGGCCTTTCGTTTTA

TCTGTTGTTTGTCGGTGAACGCTCTCCTGAGTAGGACAAA

Fig. 7

RC21 protein sequence    (SEQ ID NO: 08)

MYPDLKGKVVAITGAASGLGKAMAIRFGKEQAKVVINYYSNKQDPNEVKEEVIKAGGEAVVVQGDVTKEEDV

KNIVQTAI

KEFGTLDIMINNAGLENPVPSHEMPLKDWDKVIGTNLTGAFLGSREAIKYFVENDIKGNVINMSSVHEVIPWPL

FVHFAA

SKGGIKLMTETLALEYAPKGIRVNNIGPGAINTPINAEKFADPKQKADVESMIPMGYIGEPEEIAAVAVWLASK

ESSYVT

GITLFADGGMTKYPSFQAGRG.

Fig. 8

RC28 DNA sequence       (SEQ ID NO: 09)

ATGTATCCGGACTTAAAAGGAAAAGTCGTCGCTATTACAGGAGCTGCTTCAGGGCTCGGAAAGGCAATG
GCCATTCGCTT

CGGCAAGGAGCAGGCAAAAGTGGTTATCAACTATTATAGTAATAAACAAGATCCGAACGAGGTAAAAGA
AGAGGTCATCA

AGGCGGGCGGTGAAGCTGTTGTCGTCCAAGGAGATGTCACGAAAGAGGAAGATGTAAAAAATATCGTG
CAAACGGCAATT

AAAGAGTTCGGCACACTCGATATTATGATTAATAATGCCGGTCTTGAAAATCCTGTGCCATCTCACGAAA
TGCCGCTTAA

GGATTGGGATAAAGTCATCGGCACAAACTTAACAGGTGCCTTTTTAGGAAGCCGTGAAGCGATTAAATA
TTTCGTAGAAA

ACGATATCAAGGGAAATGTCATCAACATGTCCACCGTGCACGAAGTGATTCCTTGGCCGTTATTTGTTCA
CTACGCGGCA

AGTAAAGGCGGGATAAAGCTGATGACAGAAACATTGGCGTTGGAATACGCGCCGAAGGGCATTCGCGT
GAACAATATCGG

GCCAGGTGCGATCAATACGCCAATCAATGCTGAAAAATTTGCTGACCCTAAACAGAAAGCAGATGTAGA
AAGCATGATTC

CGATGGGGTATATCGGCGAACCGGAGGAGATCGCCGCAGTGGCAGTGTGGCTTGCTTCGAAGGAATC
CAGCTATGTTACA

GGCATCACATTGTTTGCGGACGGCGGAATGACGAAATATCCTTCTTTCCAGGCAGGCCGCGGTTAAAA
GCTTGGCTGTTT

TGGCGGATGAGAGAAGATTTTCAGCCTGATACAGATTAAATCAGAACGCAGAAGCGGTCTGATAAAACA
GAATTTGCCTG

GCGGCAGTAGCGCGGTGGTCCCACCTGACCCCATGCCGAACTCAGAAGTGAAACGCCGTAGCGCCGA
TGGTAGTGTGGGG

TCTCCCCATGCGAGAGTAGGGAACTGCCAGGCATCAAATAAAACGAAAGGCTCAGTCGAAAGACTGGG
CCTTTCGTTTTA

TCTGTTGTTTGTCGGTGAACGCTCTCCTGAGTAGGACAAA

Fig. 9

RC28 protein sequence    (SEQ ID NO: 10)

MYPDLKGKVVAITGAASGLGKAMAIRFGKEQAKVVINYYSNKQDPNEVKEEVIKAGGEAVVVQGDVTKEEDV

KNIVQTAI

KEFGTLDIMINNAGLENPVPSHEMPLKDWDKVIGTNLTGAFLGSREAIKYFVENDIKGNVINMSTVHEVIPWPL

FVHYAA

SKGGIKLMTETLALEYAPKGIRVNNIGPGAINTPINAEKFADPKQKADVESMIPMGYIGEPEEIAAVAVWLASK

ESSYVT

GITLFADGGMTKYPSFQAGRG.

Fig. 10

RC35 DNA sequence     (SEQ ID NO: 11)

ATGTATCCGGACTTAAAAGGAAAAGTCGTCGCTATTACAGGAGCTGCTTCAGGGCTCGGAAAGGCAATGGCCATTCGCTT

CGGCAAGGAGCAGGCAAAAGTGGTTATCAACTATTATAGTAATAAACAAGATCCGAACGAGGTAAAAGAAGAGGTCATCA

AGGCGGGCGGTGAAGCTGTTGTCGTCCAAGGAGATGTCACGAAAGAGGAAGATGTAAAAAATATCGTGCAAACGGCAATT

AAAGAGTTCGGCACACTCGATATTATGATTAATAATGCCGGTCTTGAAAATCCTGTGCCATCTCACGAAATGCCGCTTAA

GGATTGGGATAAAGTCATCGGCACAAACTTAACAGGTGCCTTTTTAGGAAGCCGTGAAGCGATTAAATATTTCGTAGAAA

ACGATATCAAGGGAAATGTCATCAACATGTCCACCGTGCACGAAGTGATTCCTTGGCCGTTATTTGTTCACTACGCGGCA

AGTAAAGGCGGGATAAAGCTGATGACAGAAACATTGGCGTTGGAATACGCGCCGAAGGGCATTCGCGTGAACAATATCGG

GCCAGGTGCGATCAATACGCCAATCAATGCTGAAAAATTTGCTGACCCTAAACAGAAAGCAGATGTAGAAAGCATGATTC

CGATGGGGTATATCGGCGAACCGGAGGAGATCGCCGCAGTGGCAGTGTGGCTTGCTTCGAAGGAATCCAGCTATGTTACA

GGCATCACATTGTTTGCGGACGGCGGAATGACGAAATATCCTTCTTTCCAGGCAGGCCGCGGTTAAAAGCTTGGCTGTTT

TGGCGGATGAGAGAAGATTTTCAGCCTGATACAGATTAAATCAGAACGCAGAAGCGGTCTGATAAAACAGAATTTGCCTG

GCGGCAGTAGCGCGGTGGTCCCACCTGACCCCATGCCGAACTCAGAAGTGAAACGCCGTAGCGCCGATGGTAGTGTGGGG

TCTCCCCATGCGAGAGTAGGGAACTGCCAGGCATCAAATAAAACGAAAGGCTCAGTCGAAAGACTGGGCCTTTCGTTTTA

TCTGTTGTTTGTCGGTGAACGCTCTCCTGAGTAGGACAAA

Fig. 11

RC35 protein sequence    (SEQ ID NO: 12)

MYPDLKGKVVAITGAASGLGKAMAIRFGKEQAKVVINYYSNKQDPNEVKEEVIKAGGEAVVVQGDVTKEEDV
KNIVQTAI
KEFGTLDIMINNAGLENPVPSHEMPLKDWDKVIGTNLTGAFLGSREAIKYFVENDIKGNVINMSTVHEVIPWPL
FVHYAA
SKGGIKLMTETLALEYAPKGIRVNNIGPGAINTPINAEKFADPKQKADVESMIPMGYIGEPEEIAAVAVWLASK
ESSYVT
GITLFADGGMTKYPSFQAGRG.

Fig. 12

BsGlucDH-His6 DNA sequence    (SEQ ID NO: 13)

ATGTATCCGGACTTAAAAGGAAAAGTCGTCGCTATTACAGGAGCTGCTTCAGGGCTCGGAAAGGCAATG
GCCATTCGCTT
CGGCAAGGAGCAGGCAAAAGTGGTTATCAACTATTATAGTAATAAACAAGATCCGAACGAGGTAAAAGA
AGAGGTCATCA
AGGCGGGCGGTGAAGCTGTTGTCGTCCAAGGAGATGTCACGAAAGAGGAAGATGTAAAAAATATCGTG
CAAACGGCAATT
AAAGAGTTCGGCACACTCGATATTATGATTAATAATGCCGGTCTTGAAAATCCTGTGCCATCTCACGAAA
TGCCGCTTAA
GGATTGGGATAAAGTCATCGGCACAAACTTAACAGGTGCCTTTTTAGGAAGCCGTGAAGCGATTAAATA
TTTCGTAGAAA
ACGATATCAAGGGAAATGTCATCAACATGTCCAGTGTGCACGAAGTGATTCCTTGGCCGTTATTTGTTCA
CTACGCGGCA
AGTAAAGGCGGGATAAAGCTGATGACAGAAACATTGGCGTTGGAATACGCGCCGAAGGGCATTCGCGT
GAACAATATCGG
GCCAGGTGCGATCAATACGCCAATCAATGCTGAAAAATTTGCTGACCCTAAACAGAAAGCAGATGTAGA
AAGCATGATTC
CGATGGGGTATATCGGCGAACCGGAGGAGATCGCCGCAGTGGCAGTGTGGCTTGCTTCGAAGGAATC
CAGCTATGTTACA
GGCATCACATTGTTTGCGGACGGCGGAATGACGAAATATCCTTCTTTCCAGGCAGGCCGCGGTCACCA
TCACCATCACCA
TTAA

Fig. 13

BsGlucDH-His6 protein sequence     (SEQ ID NO: 14)

MYPDLKGKVVAITGAASGLGKAMAIRFGKEQAKVVINYYSNKQDPNEVKEEVIKAGGEAVVVQGDVTKEEDV
KNIVQTAI
KEFGTLDIMINNAGLENPVPSHEMPLKDWDKVIGTNLTGAFLGSREAIKYFVENDIKGNVINMSSVHEVIPWPL
FVHYAA
SKGGIKLMTETLALEYAPKGIRVNNIGPGAINTPINAEKFADPKQKADVESMIPMGYIGEPEEIAAVAVWLASK
ESSYVT
GITLFADGGMTKYPSFQAGRGHHHHHH.

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: forward
      primer

<400> SEQUENCE: 1
ttcacacagg aaacagaatt catg                                           24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: reverse
      primer

<400> SEQUENCE: 2
tccgccaaaa cagccaagct ttta                                           24
```

```
<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: forward
      primer

<400> SEQUENCE: 3
gccatctcac gaaatgcc                                                    18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: reverse
      primer

<400> SEQUENCE: 4
attgttcacg cgaatgcc                                                    18

<210> SEQ ID NO 5
<211> LENGTH: 786
<212> TYPE: DNA
<213> ORGANISM: Bacillus subtilis

<400> SEQUENCE: 5
atgtatccgg acttaaaagg aaaagtcgtc gctattacag gagctgcttc agggctcgga      60
aaggcaatgg ccattcgctt cggcaaggag caggcaaaag tggttatcaa ctattatagt     120
aataaacaag atccgaacga ggtaaaagaa gaggtcatca aggcgggcgg tgaagctgtt     180
gtcgtccaag gagatgtcac gaaagaggaa gatgtaaaaa atatcgtgca acggcaatt     240 aaagagttcg gcacactcga tattatgatt aataatgccg gtcttgaaaa tcctgtgcca     300
tctcacgaaa tgccgcttaa ggattgggat aaagtcatcg cacaaactt aacaggtgcc     360 ttttaggaa gccgtgaagc gattaaatat ttcgtagaaa acgatatcaa gggaaatgtc     420
atcaacatgt ccagtgtgca cgaagtgatt ccttggccgt tatttgttca ctacgcggca     480
agtaaaggcg ggataaagct gatgacagaa acattggcgt tggaatacgc gccgaagggc     540
attcgcgtga acaatatcgg gccaggtgcg atcaatacgc caatcaatgc tgaaaaattt     600
gctgacccta acagaaaagc agatgtgaaa agcatgattc cgatgggta tatcggcgaa     660 ccggaggaga tcgccgcagt ggcagtgtgg cttgcttcga aggaatccag ctatgttaca     720
ggcatcacat tgtttgcgga cggcggaatg acgaaatatc cttcttttcca ggcaggccgc     780 ggttaa                                                                786

<210> SEQ ID NO 6
<211> LENGTH: 261
<212> TYPE: PRT
<213> ORGANISM: Bacillus subtilis

<400> SEQUENCE: 6

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45
```

```
Lys Glu Glu Val Ile Lys Ala Gly Gly Glu Ala Val Val Val Gln Gly
 50                  55                  60
Asp Val Thr Lys Glu Glu Asp Val Lys Asn Ile Val Gln Thr Ala Ile
 65                  70                  75                  80
Lys Glu Phe Gly Thr Leu Asp Ile Met Ile Asn Asn Ala Gly Leu Glu
                 85                  90                  95
Asn Pro Val Pro Ser His Glu Met Pro Leu Lys Asp Trp Asp Lys Val
                100                 105                 110
Ile Gly Thr Asn Leu Thr Gly Ala Phe Leu Gly Ser Arg Glu Ala Ile
            115                 120                 125
Lys Tyr Phe Val Glu Asn Asp Ile Lys Gly Asn Val Ile Asn Met Ser
    130                 135                 140
Ser Val His Glu Val Ile Pro Trp Pro Leu Phe Val His Tyr Ala Ala
145                 150                 155                 160
Ser Lys Gly Gly Ile Lys Leu Met Thr Glu Thr Leu Ala Leu Glu Tyr
                165                 170                 175
Ala Pro Lys Gly Ile Arg Val Asn Asn Ile Gly Pro Gly Ala Ile Asn
            180                 185                 190
Thr Pro Ile Asn Ala Glu Lys Phe Ala Asp Pro Lys Gln Lys Ala Asp
        195                 200                 205
Val Glu Ser Met Ile Pro Met Gly Tyr Ile Gly Glu Pro Glu Glu Ile
210                 215                 220
Ala Ala Val Ala Val Trp Leu Ala Ser Lys Glu Ser Ser Tyr Val Thr
225                 230                 235                 240
Gly Ile Thr Leu Phe Ala Asp Gly Gly Met Thr Lys Tyr Pro Ser Phe
                245                 250                 255
Gln Ala Gly Arg Gly
            260

<210> SEQ ID NO 7
<211> LENGTH: 1080
<212> TYPE: DNA
<213> ORGANISM: Artificial Sequence
<220> FEATURE:
<223> OTHER INFORMATION: Description of Artificial Sequence: GlucDH
      variant RC-21

<400> SEQUENCE: 7
atgtatccgg acttaaaagg aaaagtcgtc gctattacag gagctgcttc agggctcgga      60
aaggcaatgg ccattcgctt cggcaaggag caggcaaaag tggttatcaa ctattatagt     120
aataaacaag atccgaacga ggtaaaagaa gaggtcatca aggcgggcgg tgaagctgtt     180
gtcgtccaag gagatgtcac gaaagaggaa gatgtaaaaa atatcgtgca aacggcaatt     240
aaagagttcg gcacactcga tattatgatt aataatgccg gtcttgaaaa tcctgtgcca     300
tctcacgaaa tgccgcttaa ggattgggat aaagtcatcg gcacaaactt aacaggtgcc     360
tttttaggaa gccgtgaagc gattaaatat ttcgtagaaa acgatatcaa gggaaatgtc     420
atcaacatgt ccaccgtgca cgaagtgatt ccttggccgt tatttgttca ctacgcggca     480
agtaaaggcg ggataaagct gatgacagaa acattggcgt ggaatacgc gccgaagggc     540 attcgcgtga acaatatcgg gccaggtgcg atcaatacgc caatcaatgc tgaaaaattt     600
gctgacccta aacagaaagc agatgtagaa agcatgattc cgatggggta tatcggcgaa     660
ccggaggaga tcgccgcagt ggcagtgtgg cttgcttcga aggaatccag ctatgttaca     720
ggcatcacat tgtttgcgga cggcggaatg acgaaatatc cttctttcca ggcaggccgc     780
```

-continued

```
ggttaaaagc ttggctgttt tggcggatga gagaagattt tcagcctgat acagattaaa      840
tcagaacgca aagcggtct gataaaacag aatttgcctg gcggcagtag cgcggtggtc      900
ccacctgacc ccatgccgaa ctcagaagtg aaacgccgta gcgccgatgg tagtgtgggg      960
tctccccatg cgagagtagg gaactgccag gcatcaaata aaacgaaagg ctcagtcgaa     1020
agactgggcc tttcgtttta tctgttgttt gtcggtgaac gctctcctga gtaggacaaa     1080
```

<210> SEQ ID NO 8
<211> LENGTH: 261
<212> TYPE: PRT
<213> ORGANISM: Artificial
<220> FEATURE:
<223> OTHER INFORMATION: Description of Artificial Sequence: GlucDH variant RC-21

<400> SEQUENCE: 8

```
Met Tyr Pro Asp Leu Lys Gly Lys Val Val Ala Ile Thr Gly Ala Ala
 1               5                  10                  15

Ser Gly Leu Gly Lys Ala Met Ala Ile Arg Phe Gly Lys Glu Gln Ala
             20                  25                  30

Lys Val Val Ile Asn Tyr Tyr Ser Asn Lys Gln Asp Pro Asn Glu Val
         35                  40                  45

Lys Glu Glu Val Ile Lys Ala Gly Gly Glu Ala Val Val Val Gln Gly
     50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Phe Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Lys Tyr Pro Ser Phe
                245                 250                 255

Gln Ala Gly Arg Gly
            260
```

<210> SEQ ID NO 9
<211> LENGTH: 1080
<212> TYPE: DNA
<213> ORGANISM: Artificial Sequence
<220> FEATURE:
<223> OTHER INFORMATION: Description of Artificial Sequence: GlucDH -continued variant RC-28

<400> SEQUENCE: 9

| | | | | | |
|---|---|---|---|---|---|
| atgtatccgg | acttaaaagg | aaaagtcgtc | gctattacag | gagctgcttc | agggctcgga | 60 |
| aaggcaatgg | ccattcgctt | cggcaaggag | caggcaaaag | tggttatcaa | ctattatagt | 120 |
| aataaacaag | atccgaacga | ggtaaaagaa | gaggtcatca | aggcgggcgg | tgaagctgtt | 180 |
| gtcgtccaag | gagatgtcac | gaaagaggaa | gatgtaaaaa | atatcgtgca | aacggcaatt | 240 |
| aaagagttcg | gcacactcga | tattatgatt | aataatgccg | gtcttgaaaa | tcctgtgcca | 300 |
| tctcacgaaa | tgccgcttaa | ggattgggat | aaagtcatcg | gcacaaactt | aacaggtgcc | 360 |
| ttttaggaa | gccgtgaagc | gattaaatat | ttcgtagaaa | acgatatcaa | gggaaatgtc | 420 |
| atcaacatgt | ccaccgtgca | cgaagtgatt | ccttggccgt | tatttgttca | ctacgcggca | 480 |
| agtaaaggcg | ggataaagct | gatgacagaa | acattggcgt | tggaatacgc | gccgaagggc | 540 |
| attcgcgtga | acaatatcgg | gccaggtgcg | atcaatacgc | caatcaatgc | tgaaaaattt | 600 |
| gctgacccta | aacagaaagc | agatgtagaa | agcatgattc | cgatggggta | tatcggcgaa | 660 |
| ccggaggaga | tcgccgcagt | ggcagtgtgg | cttgcttcga | aggaatccag | ctatgttaca | 720 |
| ggcatcacat | tgtttgcgga | cggcggaatg | acgaaatatc | cttctttcca | ggcaggccgc | 780 |
| ggttaaaagc | ttggctgttt | tggcggatga | gagaagattt | tcagcctgat | acagattaaa | 840 |
| tcagaacgca | gaagcggtct | gataaaacag | aatttgcctg | gcggcagtag | cgcggtggtc | 900 |
| ccacctgacc | ccatgccgaa | ctcagaagtg | aaacgccgta | gcgccgatgg | tagtgtgggg | 960 |
| tctcccatg | cgagagtagg | gaactgccag | gcatcaaata | aaacgaaagg | ctcagtcgaa | 1020 |
| agactgggcc | tttcgtttta | tctgttgttt | gtcggtgaac | gctctcctga | gtaggacaaa | 1080 |

<210> SEQ ID NO 10
<211> LENGTH: 261
<212> TYPE: PRT
<213> ORGANISM: Artificial Sequence
<220> FEATURE:
<223> OTHER INFORMATION: Description of Artificial Sequence: GlucDH variant RC-28

<400> SEQUENCE: 10

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Thr Val His Glu Val Ile Pro Trp Pro Leu Phe Val His Tyr Ala Ala

```
                145                 150                 155                 160
Ser Lys Gly Gly Ile Lys Leu Met Thr Glu Thr Leu Ala Leu Glu Tyr
                        165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Lys Tyr Pro Ser Phe
                245                 250                 255

Gln Ala Gly Arg Gly
            260

<210> SEQ ID NO 11
<211> LENGTH: 1080
<212> TYPE: DNA
<213> ORGANISM: Artificial Sequence
<220> FEATURE:
<223> OTHER INFORMATION: Description of Artificial Sequence: GlucDH
      Variant RC-35

<400> SEQUENCE: 11
atgtatccgg acttaaaagg aaaagtcgtc gctattacag agctgcttc agggctcgga      60 aaggcaatgg ccattcgctt cggcaaggag caggcaaaag tggttatcaa ctattatagt    120
aataaacaag atccgaacga ggtaaaagaa gaggtcatca aggcgggcgg tgaagctgtt    180
gtcgtccaag gagatgtcac gaaagaggaa gatgtaaaaa atatcgtgca acggcaatt    240 aaagagttcg gcacactcga tattatgatt aataatgccg gtcttgaaaa tcctgtgcca    300
tctcacgaaa tgccgcttaa ggattgggat aaagtcatcg gcacaaactt aacaggtgcc    360
tttttaggaa gccgtgaagc gattaaatat ttcgtagaaa acgatatcaa gggaaatgtc    420
atcaacatgt ccaccgtgca cgaagtgatt ccttggccgt tatttgttca ctacgcggca    480
agtaaaggcg ggataaagct gatgacagaa acattggcgt ggaatacgc gccgaagggc    540 attcgcgtga caatatcgg gccaggtgcg atcaatacgc caatcaatgc tgaaaaattt    600
gctgacccta acagaaagc agatgtgaaa agcatgattc cgatggggta tatcggcgaa    660
ccggaggaga tcgccgcagt ggcagtgtgg cttgcttcga aggaatccag ctatgttaca    720
ggcatcacat tgtttgcgga cggcggaatg acgaaatatc cttctttcca ggcaggccgc    780
ggttaaaagc ttggctgttt tggcggatga gagaagattt tcagcctgat acagattaaa    840
tcagaacgca gaagcggtct gataaaacag aatttgcctg gcggcagtag cgcggtggtc    900
ccacctgacc ccatgccgaa ctcagaagtg aaacgccgta cgccgatgg tagtgtgggg    960 tctcccatg cgagagtagg gaactgccag gcatcaaata aaacgaaagg ctcagtcgaa   1020
agactgggcc tttcgttta tctgttgttt gtcggtgaac gctctcctga gtaggacaaa   1080

<210> SEQ ID NO 12
<211> LENGTH: 261
<212> TYPE: PRT
<213> ORGANISM: Artificial Sequence
<220> FEATURE:
<223> OTHER INFORMATION: Description of Artificial Sequence: GlucDH
      variant RC-35
```

<400> SEQUENCE: 12

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Thr Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Lys Tyr Pro Ser Phe
                245                 250                 255

Gln Ala Gly Arg Gly
                260
```

<210> SEQ ID NO 13
<211> LENGTH: 804
<212> TYPE: DNA
<213> ORGANISM: Bacillus subtilis
<220> FEATURE:
<221> NAME/KEY: misc_feature
<223> OTHER INFORMATION: BsGlucDH-His6

<400> SEQUENCE: 13

```
atgtatccgg acttaaaagg aaaagtcgtc gctattacag agctgcttc agggctcgga      60 aaggcaatgg ccattcgctt cggcaaggag caggcaaaag tggttatcaa ctattatagt    120
aataaacaag atccgaacga ggtaaaagaa gaggtcatca aggcgggcgg tgaagctgtt    180
gtcgtccaag gagatgtcac gaaagaggaa gatgtaaaaa atatcgtgca aacggcaatt    240
aaagagttcg gcacactcga tattatgatt aataatgccg gtcttgaaaa tcctgtgcca    300
tctcacgaaa tgccgcttaa ggattgggat aaagtcatcg gcacaaactt aacaggtgcc    360 ttttaggaa gccgtgaagc gattaaatat ttcgtagaaa acgatatcaa gggaaatgtc    420
atcaacatgt ccagtgtgca cgaagtgatt ccttggccgt tatttgttca ctacgcggca    480
```

```
agtaaaggcg ggataaagct gatgacagaa acattggcgt tggaatacgc gccgaagggc    540
attcgcgtga acaatatcgg gccaggtgcg atcaatacgc caatcaatgc tgaaaaattt    600
gctgacccta acagaaagc agatgtagaa agcatgattc cgatggggta tatcggcgaa     660
ccggaggaga tcgccgcagt ggcagtgtgg cttgcttcga aggaatccag ctatgttaca    720
ggcatcacat tgtttgcgga cggcggaatg acgaaatatc cttctttcca ggcaggccgc    780
ggtcaccatc accatcacca ttaa                                           804
```

<210> SEQ ID NO 14
<211> LENGTH: 267
<212> TYPE: PRT
<213> ORGANISM: Bacillus subtilis
<220> FEATURE:
<221> NAME/KEY: MISC_FEATURE
<223> OTHER INFORMATION: BsGlucDH-His6

<400> SEQUENCE: 14

```
Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Val Trp Leu Ala Ser Lys Glu Ser Ser Tyr Val Thr
225                 230                 235                 240

Gly Ile Thr Leu Phe Ala Asp Gly Gly Met Thr Lys Tyr Pro Ser Phe
                245                 250                 255

Gln Ala Gly Arg Gly His His His His His His
            260                 265
```

INACTIVATED ENZYME VARIANTS AND ASSOCIATED PROCESS AND REAGENT SYSTEM

CROSS-REFERENCE TO RELATED APPLICATION

This application is a divisional application of U.S. patent application Ser. No. 10/975,697, filed Oct. 28, 2004, now U.S. Pat. No. 7,712,890, which is incorporated herein by reference.

TECHNICAL DESCRIPTION

The present disclosure relates to oxidoreductase apoenzyme variants which are enzymatically inactive but have coenzyme-binding properties. Further, the present invention relates to DNA sequences encoding these oxidoreductase apoenzyme variants, expression vectors containing such DNA sequences and the use of these oxidoreductase apoenzyme variants in diagnostic applications.

BACKGROUND

It is known in the art to use enzymatic methods to detect analytes, for example glucose in blood. In these methods, the analyte to be detected is contacted with a detection reagent which contains a coenzyme. The coenzyme is reduced or oxidized upon enzymatic oxidation or reduction of the analyte, respectively. For highly concentrated analytes this change in the redox state of the coenzyme can be measured directly, e.g. by dual UV-wavelength measurement. However, if the concentration of the analyte and thus the concentration of the coenzyme is below about $10^{-3}$ M, enzymatic detection methods frequently require that the redox equivalents formed upon oxidation or reduction, respectively have to be transferred to mediators which are then detected electrochemically or photometrically in a further step. Enzymatic detection methods that utilize mediators require a calibration step which furnishes a direct connection between the measured value and the concentration of the analyte to be measured. In light of the above discussion, additional options for detecting analytes in a sample are desirable.

SUMMARY OF THE INVENTION

Embodiments of the invention in accordance with the present disclosure may comprise one or more of the following features or combinations thereof;

The disclosure provides a variant of an oxidoreductase apoenzyme which is (i) substantially enzymatically inactive and (ii) capable of efficiently binding a coenzyme.

The disclosure also provides a nucleic acid molecule encoding an oxidoreductase variant as described above.

The disclosure further provides, a vector comprising a DNA sequence encoding the above oxidoreductase variant. The DNA sequence may be operably linked to an expression control sequence.

In addition, the disclosure provides a host cell which is transformed with an expression vector as described above.

A variant of an oxidoreductase apoenzyme which is substantially enzymatically inactive and capable of efficiently binding to a coenzyme can be obtained by introducing mutations in the amino acid sequence of a corresponding wild type enzyme. The desired properties are obtainable by substitutions of individual amino acids and/or by fusing additional segments of several amino acids at the C terminus or the N terminus and/or by inserting such segments into the amino acid sequence of a desired oxidoreductase.

Thus, the present disclosure further provides a method for obtaining suitable variants, the method comprising
 (a) providing a DNA sequence coding for a wild-type oxidoreductase enzyme,
 (b) introducing mutations into the DNA sequence to obtain oxidoreductase variants,
 (c) selecting the variants for (i) substantial lack of enzymatic activity and (ii) capability of binding coenzyme, and identifying and isolating suitable enzymes, and
 (d) genetically characterizing and isolating the selected variants.

An oxidoreductase variant of the present disclosure is suitable for use in the determination of an analyte wherein the amount of coenzyme is indicative of the amount of analyte.

The disclosure also provides a reagent kit, comprising an oxidoreductase variant as described above and further reagents required for the determination of an analyte.

Further features and advantages of the invention will become apparent from the following discussion and the accompanying figures in which:

DESCRIPTION OF THE FIGURES

FIG. 2 shows the DNA sequence coding for wild type glucose dehydrogenase derived from *B. subtilis;*

FIG. 3 shows the protein sequence of the wild type glucose dehydrogenase derived from *B. subtilis;*

FIG. 7 shows a DNA sequence coding for GlucDH mutant RC-21;

FIG. 8 shows the protein sequence of GlucDH variant RC-21 (SEQ ID NO: 8);

FIG. 9 shows the DNA sequence coding for GlucDH variant RC-28 (SEQ ID NO: 9);

FIG. 10 shows the protein sequence of GlucDH variant RC-28 (SEQ ID NO: 10);

FIG. 11 shows the DNA sequence coding for GlucDH variant RC-35 (SEQ ID NO: 11);

FIG. 12 shows the protein sequence of GlucDH variant RC-35 (SEQ ID NO: 12);

FIG. 13 shows the DNA sequence coding for BsGlucDH-His6 (SEQ ID NO: 13);

FIG. 14 shows the protein sequence of BsGlucDH-His6 (SEQ ID NO: 14) with 6 His residues at the C-terminus.

DETAILED DESCRIPTION

Figure 1:
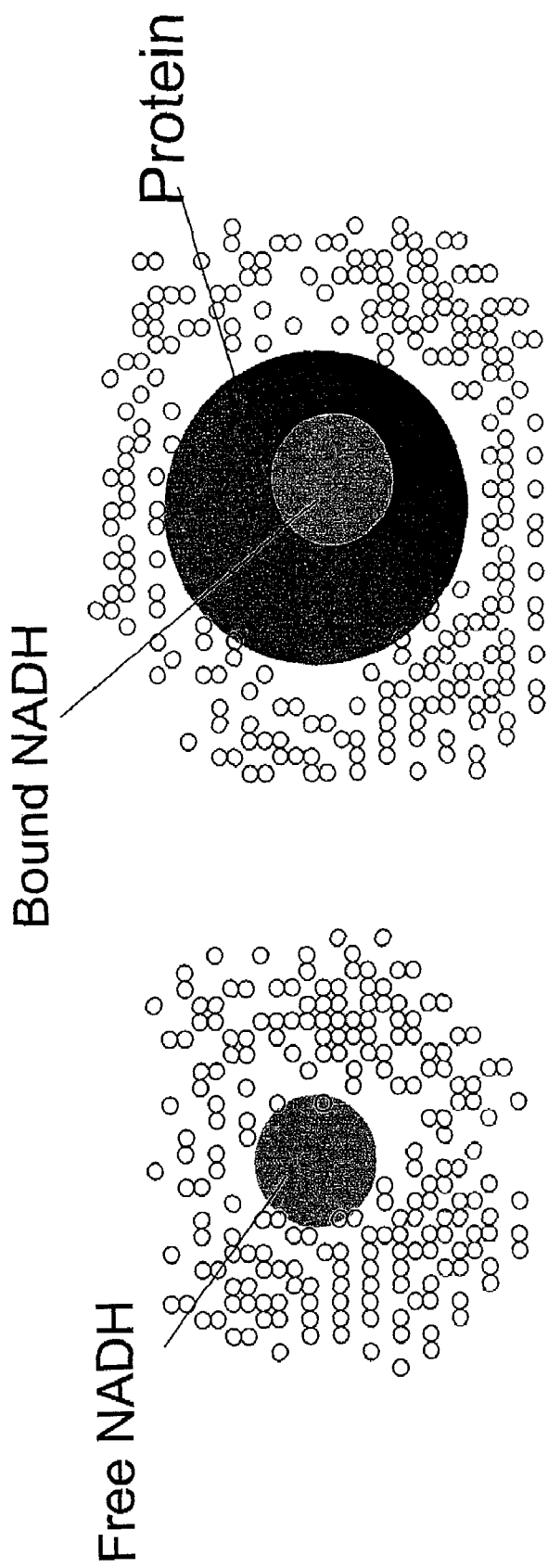
FIG. 1 illustrates the fluorescence quenching occurring with free NADH and the protection of the fluorophor NADH when surrounded by a protein.

In terms of the present disclosure, "enzymatically inactive" means that the catalytic enzymatic activity of an oxidoreductase of the present disclosure is substantially eliminated. For example, the residual enzymatic activity may be about 3% or less, such as, about 2% or about 1% the catalytic activity of the wild type enzyme. Further, "capable of efficient binding to a coenzyme" means that the variant retains about 10% or more of the coenzyme binding activity of the wild type enzyme as determined by fluorescence measurements. For example, the variant may retain about 20% or more of coenzyme binding activity of the wild type enzyme as determined by fluorescence measurements Within the meaning of the present invention, coenzymes include organic molecules which can be bound covalently or non-covalently to an enzyme. Examples of coenzymes are flavine derivatives, nicotine derivatives and quinone derivatives, for example flavine nucleoside derivatives such as FAD, $FADH_2$, FMN, $FMNH_2$, and the like, nicotine nucleoside derivatives such as $NAD^+$ (=NAD), $NADH/H^+$ (=NADH), $NADP^+$ (=NADP), $NADPH/H^+$ (=NADPH), and the like, or ubiquinones such as coenzyme Q, PQQ, and the like.

The oxidoreductase variant of the invention can be derived from any oxidoreductase. For example, D-lactate hydrogenase, glucose 6-phosphate dehydrogenase and glucose dehydrogenase may be utilized.

As mentioned above the variant of the oxidoreductase may be derived from glucose dehydrogenase. Glucose dehydrogenase (GlucDH) catalyzes the oxidation of D-glucose to D-glucono-δ-lactone in the presence of coenzyme $NAD^+$ or $NADP^+$. $NAD(P)^+$ dependent GlucDH is produced by Bacillus species during endospore formation, and has been suggested to play a role in spore germination. $NAD(P)^+$ indicates that both coenzymes $NAD^+$ or $NADP^+$ may be used. The purified enzymes from *B. cereus* (Bach, J. A. and Sadoff, H. L. (1962) Aerobic sporulation bacteria. I. Glucose dehydrogenase of *Bacillus cereus*. J. Bacteriol. 83, 699-707), *B. megaterium* M1286 (Pauly, H. E. and Pfleiderer, G. (1975) D-Glucose dehydrogenase from *Bacillus megaterium* M 1286: purification, properties and structure. Hoppe-Seyler's Z. Physiol. Chem. 356, 1613-1623), *B. megaterium* IAM1030 (Mitamura, T., Evora, R. V., Nakai, T., Makino, Y., Negoro, S., Urabe I., and Okada, H. (1990) Structure of isozyme genes of glucose dehydrogenase from *Bacillus megaterium* IAM1030. J. Ferment. Bioeng. 70, 363-369, Nagao, T., Mitamura, T., Wang, X. H., Negoro, S., Yomo, T., Urabe, I., and Okada, H. (1992) Cloning, nucleotide sequences and enzymatic properties of glucose dehydrogenase isozymes from *Bacillus megaterium* IAM1030. J. Bacteriol. 174, 5013-5020), and *B. subtilis* (Makino, Y., Ding, J.-Y., Negoro, S., Urabe, I., and Okada, H. (1989) Purification and characterization of new glucose dehydrogenase from vegetative cells of *Bacillus megaterium*. J. Ferment. Bioeng. 67, 372-379;, Lampel, K. A., Uratani, B., Chuadhry, G. R., Ramaley, R. F., and Rudikoff, S. (1986) Characterization of the developmentally regulated *Bacillus subtilis* glucose dehydrogenase gene. J. Bacteriol. 166, 238-243) have been characterized, and the GlucDH genes from *B. subtilis* and from different strains of *B. megaterium*, M1286 (Ramaley, R. F. and Vasantha, N. (1983) Glycerol protection and purification of *Bacillus subtilis* glucose dehydrogenase. J. Biol. Chem. 258, 12558-12565., Heilmann, H. J., Mägert, H. J., and Gassen, H. G. (1988) Identification and isolation of glucose dehydrogenase genes of *Bacillus megaterium* M 1286 and their expression in *Escherichia coli*. Eur. J. Biochem. 174, 485-490.), IWG3 (Makino, Y., Negoro, S., Urabe, I., and Okada, H. (1989) Stability-increasing mutants of glucose dehydrogenase from *Bacillus megaterium* IWG3. J. Biol. Chem. 264, 6381-6385.

Mitamura, T., Urabe, I., and Okada, H. (1989) Enzymatic properties of isozymes and variants of glucose dehydrogenase from *Bacillus megaterium*. Eur. J. Biochem. 186, 389-393), and IAM1030 (Nagao, T., Mitamura, T., Wang, X. H., Negoro, S., Yomo, T., Urabe, I., and Okada, H. (1992) Cloning, nucleotide sequences and enzymatic properties of glucose dehydrogenase isozymes from *Bacillus megaterium* IAM1030. J. Bacteriol. 174, 5013-5020), have been cloned and the corresponding expressed enzymes characterized.

A glucose dehydrogenase variant of the present disclosure may be derived from any wild-type $NAD(P)^+$ dependent glucose dehydrogenase. Suitable wild-type enzymes occur in different organisms, e.g. gram-positive bacteria such as Bacillus species, including *B. cereus, B. megaterium* and *B. subtilis*.

Once bound to a glucose dehydrogenase variant according to the present disclosure, the coenzyme NAD(P)H can be determined by fluorescence measurement. This is possible because this binding results in a suppression of fluorescence quenching otherwise caused by quenching molecules in too close a proximity to NAD(P)H. This suppression of quenching results in an increase of fluorescence (FIG. 1). This effect is useful for the determination of an analyte, e.g. glucose, in an assay system wherein the amount of coenzyme bound to a variant according to the present disclosure, e.g. NAD(P)H present or generated in the sample to be tested, corresponds to the amount of the analyte to be determined.

As mentioned above, one example of a wild-type enzyme from which suitable variants may be derived is the glucose dehydrogenase from *B. subtilis* (BsGlucDH), the sequence of which is shown in FIG. 3 (SEQ ID NO: 6). The catalytic activity of an oxidoreductase such as GlucDH, can be eliminated by introducing mutations/alterations in the amino acid sequence of the enzyme. Examples of such mutations include, deletion(s), insertion(s) and substitution(s) of individual amino acids, or segments containing several amino acids. Introducing these alterations result in obtaining enzyme variants which are rendered enzymatically inactive while being capable of efficient binding to a coenzyme.

In one particular example the enzyme is rendered enzymatically inactive by introducing sequence alteration(s) within a region of the enzyme, for example, defined by amino acid residues 140-165. As previously mentioned examples of these alterations include deletion(s), insertion(s), and substitution(s). In one particular example, these alterations can be introduced within the region of the enzyme defined by amino acid residues 140-146. In another particular example, these alterations can be introduced in the region of the enzyme defined by amino acid residues 155-163. In another specific example, the enzyme BsGlucDH is rendered enzymatically inactive while being capable of efficient binding to a coenzyme by introducing alterations in one or both of the regions of the enzyme defined by amino acid residues 140-146 and 155-163. It is contemplated that introducing such alterations in a corresponding region of another oxidoreductase enzyme will result in the enzyme being rendered enzymatically inactive while being capable of efficient binding to a coenzyme. Note that within the amino acid sequence of an oxidoreductase enzyme a single amino acid may be altered, e.g. substituted or two or more amino acids may be altered, e.g. substituted, as long as the desired properties are obtained.

In the case of BsGlucDH, any one of, or both of amino acid positions 145 and 158 may be substituted. For example, the serine in position 145 can be replaced by a different amino acid, e.g. threonine. Furthermore, the tyrosine position 158 can be replaced by a different amino acid, e.g. phenylalanine. Corresponding mutations may be carried out in other GlucDH species such as in GlucDH isolated from *Bacillus megaterium* strains M1286, IWGG3, IAM1030 and IFO12108 (Itoh N, Wakita, R. 2004, *Bacillus megaterium*

IFO12108 glucose dehydrogenase, EP1382683-A2), respectively. Examples of suitable variants of BsGlucDH are the proteins which have the sequences as shown in SEQ ID NOS: 8, 10 or 12. Further variants of BsGlucDH or GlucDH species from other organisms may be identified by suitable screening methods as described below, e.g. by mutagenic PCR.

Furthermore, enzyme variants having the desired properties as discussed herein are obtainable by fusing an amino acid segment containing several amino acids capable of forming a metal chelate to an amino acid sequence of an oxidoreductase. For example, an amino acid segment capable of forming a metal chelate may be chemically bound to either or both of the C terminus and N terminus of the protein sequence of an oxidoreductase and, in particular, of a glucose dehydrogenase. The additional segment, however, can also be inserted into the amino acid sequence of the glucose dehydrogenase, as long as the desired properties are maintained. The additional segment is capable of forming chelate complexes with metal ions, and thus includes a plurality of amino acids with side chains capable of chelate formation. In a further possibility the peptide capable of forming a metal chelate complex will comprise a so-called His-tag at its C-terminal end which allows for an easy purification by well established chromatographic methods, e.g. use of hexa-His and Ni-NTA-chromatography. For example, the addition of a plurality, e.g. 6 histidine residues at one or both of the C terminus and N terminus of the wild-type enzyme or a variant thereof results in the formation of a coenzyme binding enzyme without catalytic activity. The amino acid sequence of a particularly suitable variant BsGlucDH-His6 is shown in SEQ ID NO: 14.

Even though the mutations described in the present disclosure refer particularly to BsGlucDH, it is to be understood that they can also be used to modify corresponding sequence positions of other oxidoreductases e.g. other GlucDH. Such amino acid substitutions may be made on the basis of, for example, similarity in polarity, charge, solubility, hydrophobicity, hydrophilicity and the amphipathic nature of the residues involved.

The present disclosure also relates to a DNA molecule encoding an oxidoreductase variant such as a glucose dehydrogenase variant which is (i) substantially enzymatically inactive and (ii) capable of efficiently binding a coenzyme.

In one example, a glucose dehydrogenase variant is involved, and the DNA molecule comprises
    (a) a nucleotide sequence as shown in any of SEQ ID NOs: 7, 9, 11 or 13;
    (b) a nucleotide sequence which encodes the same protein as (a) but differs therefrom because of the degeneration of the genetic codes; or
    (c) a nucleotide sequence corresponding to the sequence of (a) or (b) which is derived from a different species.

The identification of further oxidoreductase (e.g. GlucDH) coding sequences from suitable sources, e.g. microorganisms as well as the purification, characterization, and cloning of relevant DNA sequences may be carried out based on the use of either primer or probe sequences, or a combination of these, derived from known oxidoreductase (GlucDH) sequences, for example from GlucDH sequences derived from Bacillus species. These primers and probes are selected from conserved sequence portions in the GlucDH sequence and are capable of hybridizing under stringent conditions to the further GlucDH sequences. Examples of stringent conditions include detecting a positive hybridization signal after washing for 1 h with 1×SSC and 0.1% SDS at temperatures between 50° C. and 65° C., for example 55° C., 62° C. or 65° C. Particular examples of stringent conditions include washing for 1 h with 0.2×SSC and 0.1% SDS at temperatures such as 50° C., 55° C., 62° C. or 65° C.

Further, the present disclosure relates to a vector comprising a nucleic acid sequence coding for an oxidoreductase variant such as a glucose dehydrogenase variant. In one aspect of the disclosure, the vector includes a DNA sequence derived from *B. subtilis* wild type GlucDH. The vector may be a prokaryotic or eukaryotic vector. The vector may be an episomal vector or a vector capable of integration into the host cell genome. Examples of vectors are plasmids, cosmids, bacteriophage or viral vectors and artificial chromosomes.

In one instance, the vector is an expression vector wherein the coding sequence is operably linked to a promoter sequence which is capable of directing its expression in a host cell. The expression vector of the invention may further comprise an origin of replication and/or a transcription termination sequence.

Expression vectors may contain further genetic elements, e.g. an origin of replication, a promoter located in front (i.e. upstream of) the DNA sequence and followed by the DNA sequence coding for all or part of oxidoreductase variants such as, in particular, GlucDH variants. The coding DNA sequence may be followed by transcription termination sequences and the remaining vector sequences. It is also possible that the expression vectors may also include either DNA sequences known in the art. For example, they may further include stability leader sequences which -provide for the stability of the expression product; secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, and sequences which provide sites for cleavage by restriction endonucleases.

It is understood that the characteristics of the actual expression vector used must be compatible with the host cell which is to be employed. For example, when cloning in an *E. coli* cell system, the expression vector should contain promoters which are operative in *E. coli* cells (e.g., tac, lac, or trp).

Suitable origins of replication for use in *E. coli* hosts include, for example, a ColE1 plasmid replication origin. Suitable promoters include, for example, the tac, lac, and trp. It is also preferred that the expression vector includes a sequence coding for a selectable marker. The selectable marker is preferably antibiotic resistance. As selectable markers, ampicillin resistance, or kanamycin resistance may be conveniently employed.

Suitable expression vectors containing the desired coding and control sequences may be constructed using standard recombinant DNA techniques as described in Sambrook et al. ("Molecular Cloning: A Laboratory Manual" (1989), Cold Spring Harbour, N.Y., Cold Spring Harbour Laboratory Press) and Ausubel, F., et al. in ("Current Protocols in Molecular Biology" (1994) John Wiley and Sons, Inc.).

This disclosure also relates to a host cell comprising an expression vector disclosed herein, operably linked to a promoter sequence. The host cells are preferably transformed with an expression vector which comprises a DNA sequence encoding an oxidoreductase variant such as a GlucDH variant, for example. Preferred host cells include, for example, *E. coli*. e.g. the strains *E. coli* HB101 (ATCC 33694) available from Promega (2800 Woods Hollow Road, Madison, Wis., USA) and XL1-Blue available from Stratagene (11011 North Torrey Pine Road, La Jolla, Calif., USA), and other prokaryotic host cells.

Expression vectors may be introduced into host cells by various methods. For example, transformation of host cells with expression vectors can be carried out by polyethylene glycol mediated protoplast transformation method (Sambrook, et al. 1989). However, other methods for introducing expression vectors into host cells, for example, electroporation, ballistic injection, or protoplast fusion, can also be employed.

Further, the present invention relates to a method of obtaining improved oxidoreductase variants and preferably improved glucose dehydrogenase variants. For optimizing protein functions, several approaches may be used. One approach does not require specific knowledge about the enzyme itself, only about the parameters to be optimized. One screening approach is to use both mutation and crossover procedures synchronously to screen populations of variant molecules in parallel for specific optimized parameters.

More particularly, new oxidoreductase variants which are substantially enzymatically inactive and capable of efficiently binding a coenzyme are obtained by a method comprising:
 (a) providing a DNA sequence coding for a wild-type oxidoreductase (glucose dehydrogenase) enzyme,
 (b) introducing mutations to obtain oxidoreductase (glucose dehydrogenase) variants, e.g. introducing random point mutations into the sequence or a predetermined portion thereof, preferably by mutagenic PCR;
 (c) selecting the variants for (i) substantial lack of enzymatic activity and (ii) capability of binding coenzyme, and identifying and isolating suitable enzymes, and
 (d) genetically characterizing and isolatine the selected variants.

The predetermined portion in step (b) may have a length of 15-50 nucleotides, wherein single or multiple random point mutations may be introduced.

Step (c) may include a determination of catalytic activity and coenzyme binding properties in a single assay, for example in a fluorescence-based assay.

The oxidoreductase variants of the invention can be used for the determination of an analyte, wherein the amount of coenzyme, e.g. NAD(P)H, is indicative of the amount of analyte.

According to one embodiment, the oxidoreductase variants are useful in a method for detecting an analyte in a sample, comprising
 (a) contacting the sample suspected to contain the analyte with a reagent comprising a variant of an oxidoreductase apoenzyme as described above, under conditions wherein the amount of coenzyme bound to the variant is indicative of the amount of analyte to be determined,
 (b) detecting the coenzyme-oxidoreductase variant complex.

The embodiments of the present invention make it possible to qualitatively or quantitatively determine analytes in a simple manner. Methods described herein are suitable for detecting any analyte which can be detected by means of an enzymatic redox reaction involving a coenzyme.

The detection reagent contains an oxidoreductase variant of the disclosure in a quantity which is sufficient to enable the detection of the analyte, in accordance with the desired test format. The analyte may be determined qualitatively and/or quantitatively. Since in one method according to the disclosure, the coenzyme is detected directly, it is not necessary for mediators or other substances which can bring about regeneration of the coenzyme to be present. These methods and the detection system make it possible to use very small quantities of sample, for example, sample volumes of <1 ml, or even <0.1 ml. Where appropriate, the sample can also be diluted before being brought into contact with the detection reagent. Further, very low concentrations of a coenzyme can be detected by the method of the invention. For example, it is possible to determine analytes present in a concentration $<10^{-4}$ M or $<10^{-5}$ M. These methods can be carried out without using mediators and/or dyes.

Examples of oxidoreductase variants for use in the detection methods are glucose dehydrogenase variants and, for example, those having the sequence as shown in any of SEQ ID NOs 8, 10, 12 or 14.

The analyte which is detected by the methods disclosed may be the coenzyme itself, e.g. $NAD(P)H/H^+$. The coenzyme, e.g. $NAD(P) H/H^+$, may also be generated by a precedent enzymatic reaction of the analyte with a precursor of the coenzyme, e.g. $NAD(P)^+$.

As the skilled person will appreciate, an inactive variant of an oxidoreductase may be used in any enzymatic assay in which the same coenzyme is used by the enzyme on which this enzymatic procedure is based.

Thus, any biological or chemical substance which can be determined by means of enzymatic reaction can be chosen as analyte, for example, an enzyme or an enzyme substrate. Examples of suitable analytes are glucose, lactic acid, malic acid, glycerol, alcohol, cholesterol, triglyceride, ascorbic acid, cysteine, glutathione, peptides, etc.

One application of the improved oxidoreductase variants described herein is the use in test strips to monitor analyte concentrations in biological samples, e.g. in samples from patients via determination of NAD(P)H without quenching. Body fluids like serum, plasma, intestinal fluid or urine are examples of sources for such samples.

The oxidoreductase variants can also be used as biosensors for monitoring NAD(P)H concentrations in a reaction vessel or a reactor.

In principle, the coenzyme bound in the variant oxidoreductase apoenzyme/coenzyme complex can be detected in any desired manner. For example, optical methods may be used for the detection. Optical detection methods include, for example, the measurement of absorption, fluorescence, circular dicroism (CD), optical rotary dispersion (ORD) and refractometry. In particular, fluorescence measurement is highly sensitive and makes it possible to detect even low concentrations of the analyte in miniaturized systems.

The method or detection system according to the invention can comprise a liquid assay with the reagent being present, for example in the form of a solution or suspension in an aqueous or non-aqueous liquid or as a powder or lyophilisate. However, the method and detection system may include a dry assay with the reagent being applied to a support. The support can include, for example, a test strip which includes an absorbent and/or swellable material which is wetted by the sample liquid to be investigated. Examples thereof are the matrices and detection methods described in PCT/EP03/05177.

Further, the disclosure relates to a reagent for the determination of an analyte in a sample, comprising an oxidoreductase variant such as a glucose dehydrogenase variant as indicated above.

Furthermore, the present disclosure relates to a reagent kit for the determination of an analyte in a sample comprising an oxidoreductase variant such as a glucose dehydrogenase variant as indicated above and further reagents required for the determination of the analyte.

The reagent and reagent kit may be components of a liquid or dry assay. For example, they may be components of a test strip.

The above description will now be explained by way of the following example.

EXAMPLES

All reagents, restriction enzymes, and other materials were obtained from Roche Diagnostics, unless specified from other commercial sources, and used according to the indication by suppliers. Operations employed for the purification, characterization and cloning of DNA can be adapted from published literatures.

1. Cloning and Expression of *Bacillus subtilis* Glucose Dehydrogenase (BsGlucDH) gene in *E. coli*

The BsGlucDH gene was amplified from *B. subtilis* genome with PCR. Both the amplified DNA fragment and the pKK-T5 plasmid were digested with the restriction enzymes EcoRI and HindIII. The digested products were gel purified and ligated. An aliquot of the ligation reaction mixture was used to transform competent *E. coil* cells, for example *E. coli* XL1 Blue cells. The transformants were subsequently selected on LB plates containing ampicillin. To assay, individual colonies were chosen, grown over night in LB medium (cf. Sambrook et al., 1989, supra) containing ampicillin and subjected to screening.

2. Mutating the Wild-Type *Bacillus subtilis* Glucose Dehydrogenase

In order to obtain mutant enzymes with desired properties, mutagenic PCR was used to generate BsGlucDH. Mutagenic PCR is a method to introduce random point mutations into the selected DNA. This method was performed according to the protocol described by Cadwell and Joyce (Cadwell, R. C. Joyce, G. F., PCR Methods Appl 3 (1994) 136-40) with some modifications. These modifications included different concentrations of primers, higher concentration of $MgCl_2$ and different concentrations of $MnCl_2$ as specified below. The Mutagenic PCR was set up as following:

| | |
|---|---|
| Template DNA | 60 fmol |
| Forward Primer | 40 pmol |
| Reverse Primer | 40 pmol |
| 10 × Taq Puffer | 10 µl (without $Mg^{2+}$; Roche # 1 699 105) |
| $MgCl_2$ | 7 mM |
| $MnCl_2$ | 0-0.8 mM |
| dATP, dGTP | 0.2 mM (Roche #1 969 064) |
| dCTP, dTTP | 1 mM (Roche # 1 969 064) |
| Taq DNA polymerase | 5 U (Roche #1 418 432) |

$H_2O$ added to total volume of 100 µl

The PCR cycling was done with the following conditions:
5 min 95° C.,
1 min 95° C.,
1 min 50° C.,
1 min 72° C.
(30 cycles),
5 min 72° C.

The product was kept at 4° C. before analysis of the product or cloning steps using this product were performed.

Forward primer was EF1 (5' TTC ACA CAG GAA ACA GAA TTC ATG 3') (SQ ID No. 1) and reverse primer was HR1 (5' TCC GCC AAA ACA GCC AAG CTT TTA 3') (SEQ ID NO: 2). Each round of mutagenic PCR was performed with $MnCl_2$ concentrations of 0, 0.1, 0.2, 0.3, 0.4, 0.5, 0.6, 0.7, or 0.8 mM $MnCl_2$ to obtain different mutagenic rates and therefore different mutated clones.

Mutagenic PCR products were purified using ion exchange techniques (Roche High Pure® PCR Product Purification Kit # 28104) and were eluted in $H_2O$. The purified PCR products and plasmid pKK-T5 were digested with restriction enzymes EcoRI and HindIII, purified by preparative gel electrophoresis (1% agarose/TAE) and gel extraction with QlAquick Gel Extraction Kit (Quiagen Cat. #28706). EcoRI/HindIII-digested PCR products were ligated into EcoRI/Hind III-digested plasmid vector pKK-T5 using T4 DNA ligase (Roche # 481 220) according to the supplier's manual. Ligation reactions were introduced into *E. coli* HB101 according to the manual for high-efficiency transformation by electroporation (Current protocols in molecular biology, chapter 1.8.4) or into *Epicurian Coli®* XL1-Blue super competent cells (Stratagene # 200236) according to the supplier's manual. Transformants were plated on LB-Agar with 100 µg/ml ampicillin and grown at 37° C., 14 h.

3. Assay and Screening of *Bacillus subtilis* Glucose Dehydrogenase and its Variants The enzymatic activity assay for BsGlucDH and its variants was performed by using glucose as substrate and a coupled enzymatic reaction.

The reaction mixture was set up by combining the following reagents:
1. 2.7 ml of 0.2 M NaCl+0.1 M Tris buffer, pH 8.5
2. 0.2 ml of 1.1 M glucose
3. 0.10 ml of 15 mM $NAD^+$
4. 0.05 ml of enzyme sample The assay for GlucDH was carried out at 25° C., and at the wavelength of 340 nm for 5 min. ΔE was calculated from the measurement points of 1 to 5 min.

$$GlucDH \text{ enzymatic activity} = \frac{3.05}{\varepsilon \times 1 \times 0,05}$$

$$\Delta A/\min[\text{sample U/ml-Solution}]$$

$$\varepsilon 340 = 6, 3[l \times mmol^{-1} \times cm^{-1}]$$

Screening clones of BsGlucDH and its variants was carried out according to the above assay procedure. Each screening step was performed in 96-well microtiter plates (MTPs). Colonies were picked into these plates and grown for 24 h in 200 µl of LB-medium (cf. Sambrook et al., 1989, supra). These plates are called master plates. From each master plate, 90 µl sample/well was transferred to a MTP containing 10 µl reagent B per/well (Bacterial Protein Extraction Reagent Pierce No. 78248) for cell disruption. The MTP was incubated at 25° C. for 15 min.

From the working plate 2×10 µl sample/well were transferred to two empty MTPs. After that, one was tested for BsGlucDH enzymatic activity in the presence of glucose and $NAD^+$. The other plate was used to measure the fluorescence intensity in the presence of NADH.

In order to screen for BsGlucDH variants showing a fluorescence signal, a first determination of the crude enzyme extract thus obtained was carried out. Using a fluorescence intensity determination reagent containing NADH, the fluorescence signal of the same samples was again determined. Any clone showing high fluorescence signal was selected as a candidate mutant.

Figure 4:
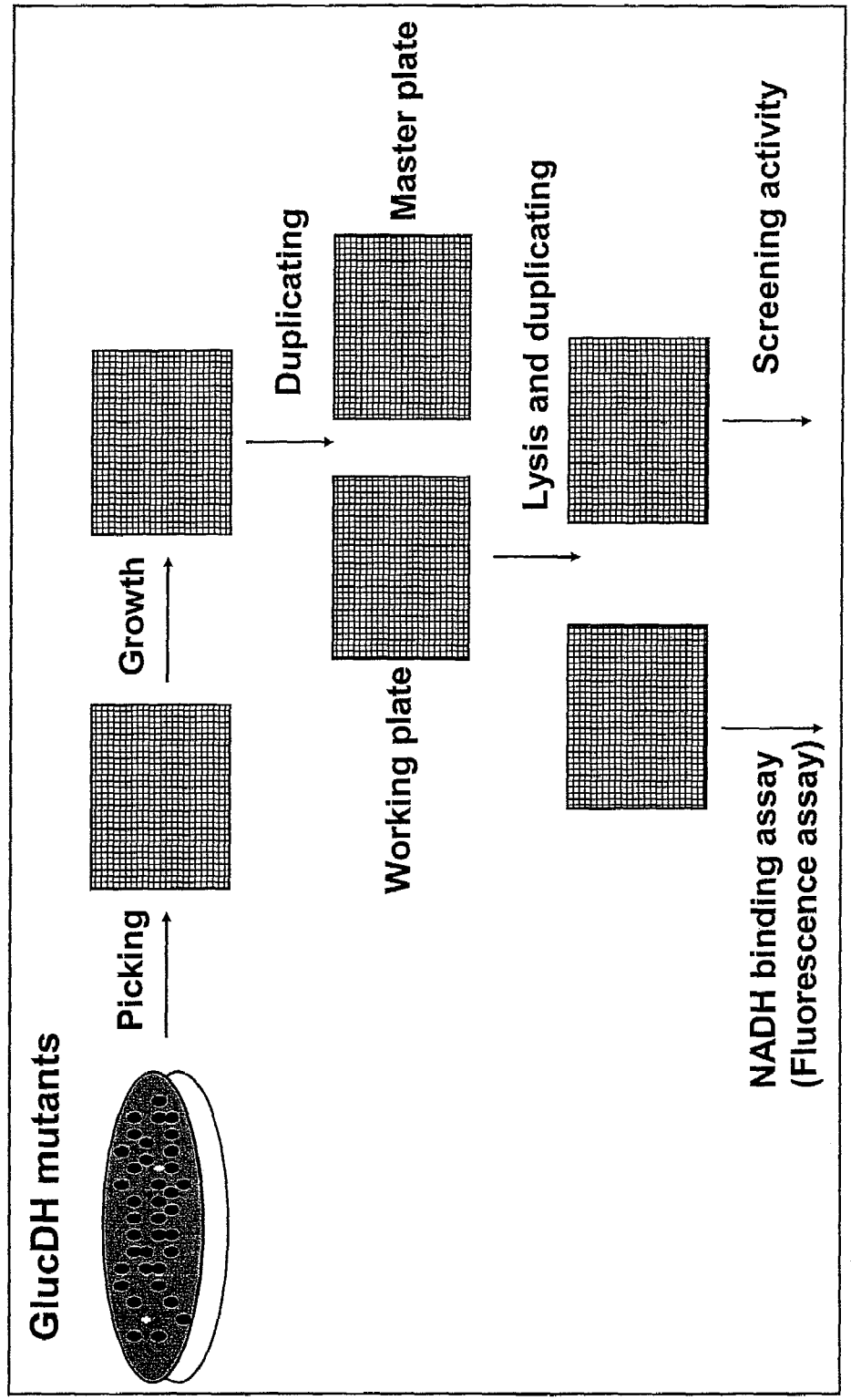
FIG. 4 shows the screening of GlucDH mutants.
Figure 5:
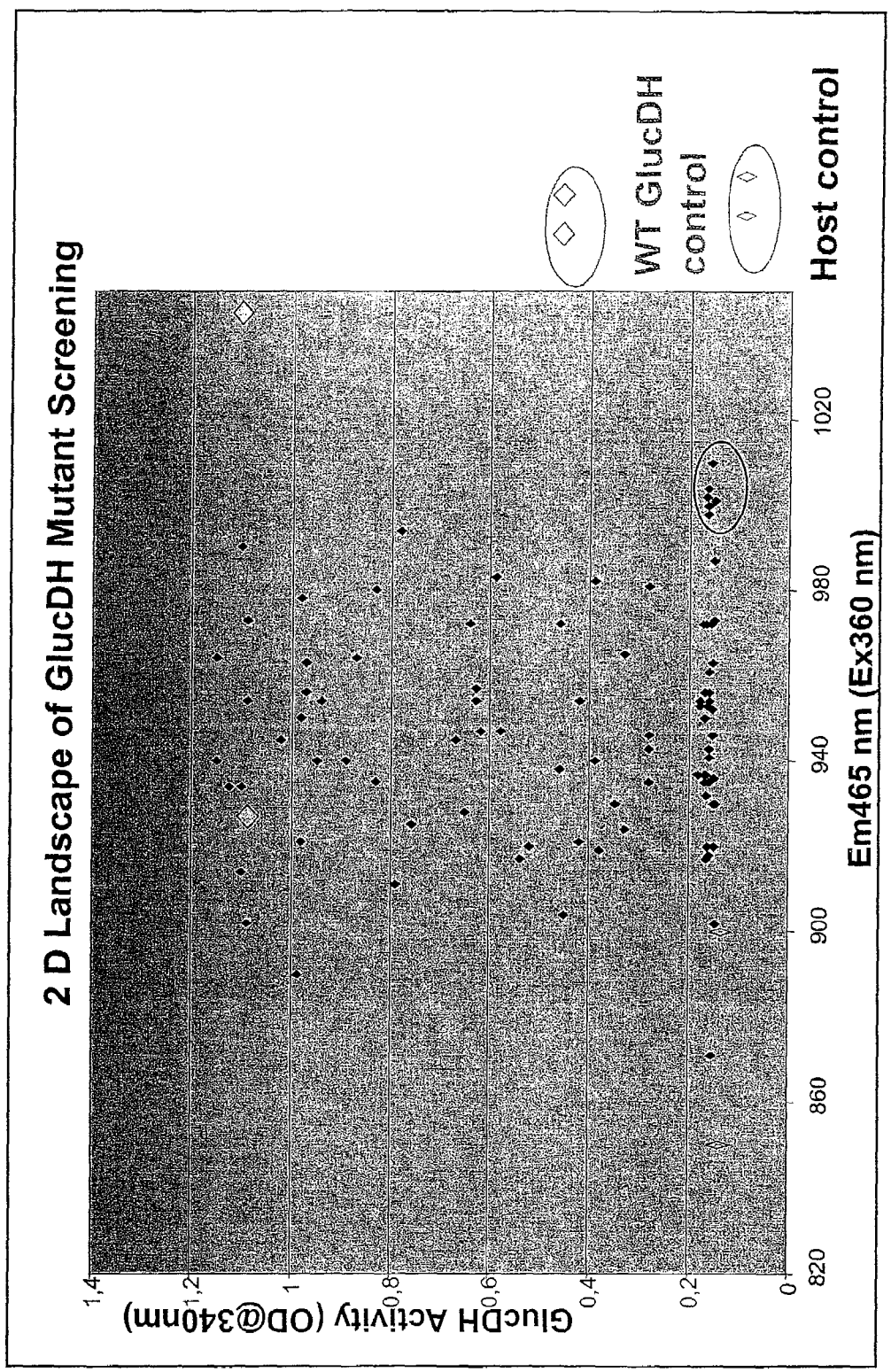
FIG. 5 shows the result of GlucDH mutant screening depicted in the form of a two dimensional landscape.

A two dimensional landscape can be plotted. The first dimension corresponds to the GlucDH enzymatic activity of each clone, and the second dimension corresponds to the corresponding fluorescence signal of each clone. Any clone which has no GlucDH enzymatic activity but a strong fluorescence signal is a candidate clone. (FIG. 4-5)

Figure 6:
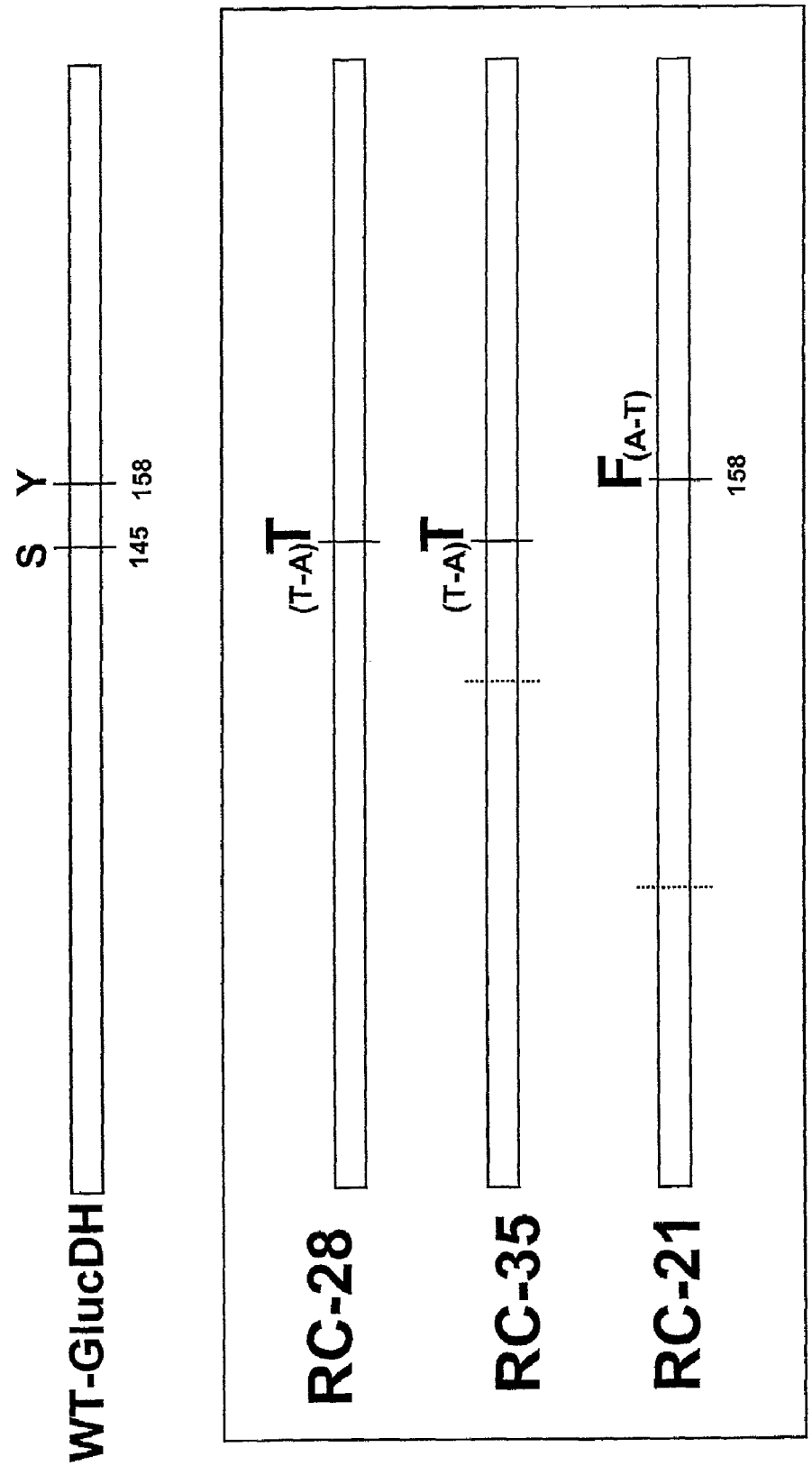
FIG. 6 shows genetic analyses of the GlucDH mutants RC-28, RC-35 and RC-21, compared to wild type GlucDH.

4. Mutants of *Bacillus subtilis* Glucose Dehydrogenase with Desired Properties The above mentioned 2D-screening efforts led to several BsGlucDH mutants with strong fluorescence signal in the presence of NADH but without glucose dehydrogenase enzymatic activity at all. The sequence alterations in these variants are shown in FIG. 6.

5. Genetic Characterization of BsGlucDH Mutants with Desired Properties

The plasmid containing the mutant BsGlucDH gene and its variants were isolated (High Pure Plasmid Isolation Kit, Roche 1754785) and sequenced using an ABI Prism Dye Terminator Sequencing Kit and ABI 3/73 and 3/77 sequencer (Amersham Pharmacia Biotech). The following primers were used:

T5 forward primer 5'-GCC ATC TCA CGA AAT GCC-3' (SEQ ID NO: 3)

T5 reverse primer 5'-ATT GTT CAC GCG AAT GCC-3' (SEQ ID NO: 4)

Preferred BsGlucDH mutants with improved properties were genetically characterized. The DNA and corresponding amino acid sequences are given in FIGS. 7-12. Amino acid substitutions of the BsGlucDH variants with desired properties are mutations: Y158F in mutant RC21 (SEQ ID NOs 7/8), S145T in mutants RC28 (SEQ ID NOs 9/10) and RC35 (SEQ ID NOs 11/12). The wild-type BsGlucDH and RC21, RC28, and RC35 with 6 His residues at the C-terminus were also generated. These enzymes were designated GlucDH-His6, RC21-His6, RC28-His6 and RC35-His6. The DNA and corresponding amino acid sequence of the His6-wild type enzyme (SEQ ID NOs 13/14) are given in FIGS. 13 and 14.

6. Purification of the BsGlucDH variants RC21, RC28 and RC35

The isolation and purification of BsGlucDH and BsGlucDH variants as selected above from cell cultures can be carried out by any known method, such as the following. After the cells were cultured in a nutrient medium, they were recovered by centrifugation. The cell pellets were homogenized in 20 mM Tris-HCl (pH 8) using high pressure cell disruption at a pressure of 900 bars to give a crude cell extract. The cell extract containing the enzyme was precipitated with Polymin G20 (0.4%), and subsequently precipitated with 2.0 M $(NH_4)_2SO_4$. The extract was then subjected to phenyl sepharose column chromatography (Pharmacia Biotech) to give a standard purified enzyme product. Usually, the end product thus obtained was at least 90% pure and shows one predominant band in SDS-PAGE corresponding to BsGlucDH. In case SDS PAGE should occasionally reveal a lower degree of purity the purification steps may be repeated.

7. Characterization of BsGlucDH and its Variants

The characterizations of BsGlucDH and its variants included a) determination of the enzymatic activity in the presence of NAD, and b) determination of the fluorescence signal in the presence of NADH.

a) Determination of the enzymatic activity in the presence of NAD

For determination of the enzymatic activity, the purified enzyme or enzyme mutant was assayed according to the assay procedure described in Example 3 b) Determination of the fluorescence signal in the presence of NADH

The determination of the fluorescence signal in the presence of NADH was done with purified enzyme or enzyme mutants. The enzyme or enzyme mutant was used at a concentration of $1.0 \times 10^{-5}$ M. NADH was added at a concentration of $1.0 \times 10^{-5}$ M. The incubations were carried out in 0.2 M NaCl+0.1 M Tris buffer at pH 8.5. The fluorescence measurement was set up as the following: Excitation at 360 nm, Emission at 465 nm, 10 reading cycles with an interval of 5 seconds between each cycle.

Figure 15:
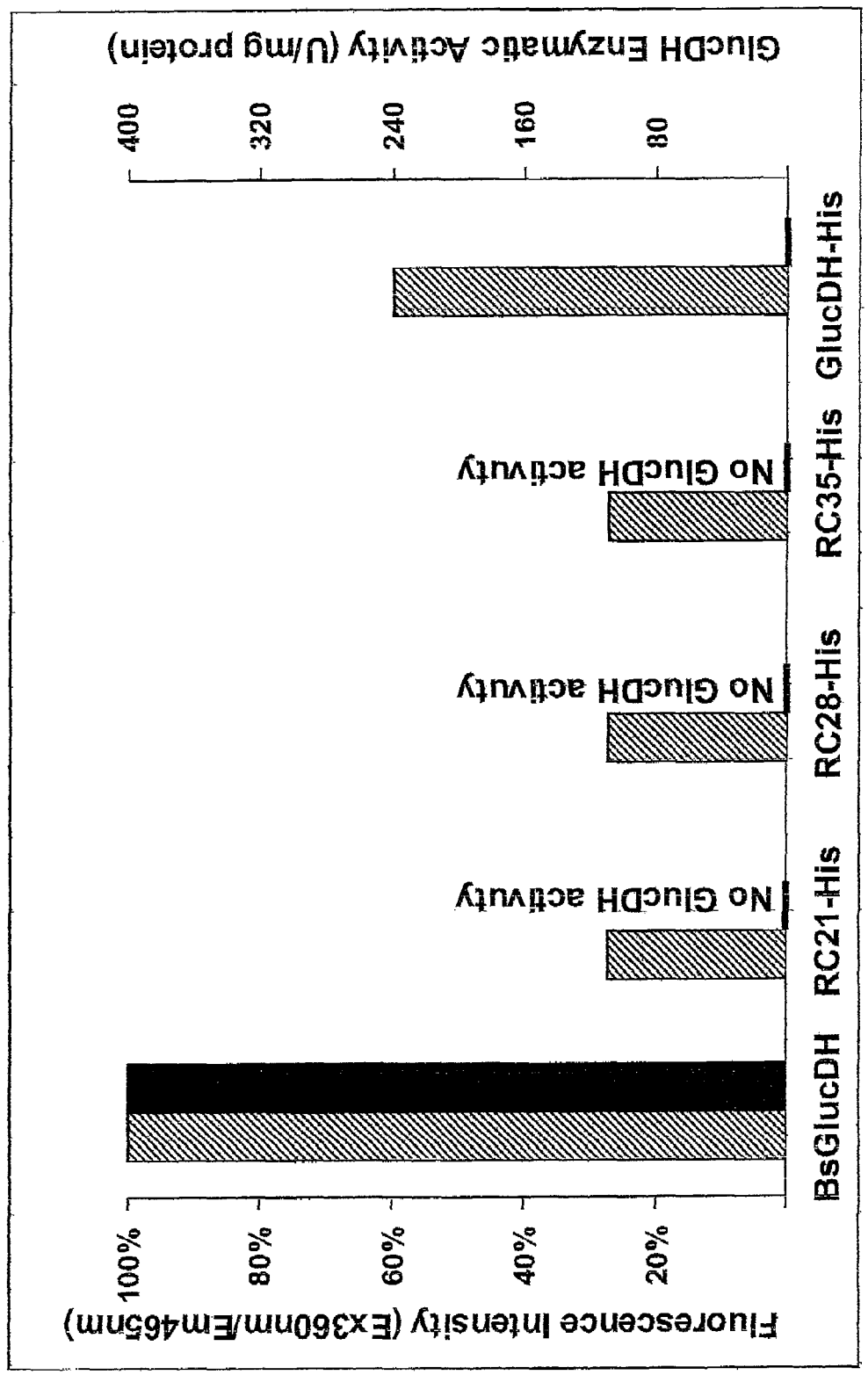
FIG. 15 shows a graph of fluorescence intensity and GlucDH enzymatic activity of BsGlucDH, RC-21-His, RC-28-His, RC-35-His and GlucDH-His.

As shown in FIG. 15, all mutants RC21-His6, RC28-His6, RC35-His6 and GlucDH-His6 have no glucose dehydrogenase enzymatic activity at all, but at the same time can still bind to NADH and give a strong fluorescence signal.

All references referred to in this disclosure are expressly incorporated herein.

The invention claimed is:

1. A method for the determination of an analyte in a sample, comprising:
   (a) providing a reagent comprising a glucose dehydrogenase variant of SEQ ID NO: 6, wherein said variant differs from SEQ ID NO: 6 by an amino acid substitution at position 145 or 158, said variant having less than 3% residual enzymatic activity relative to the wild type enzyme of *B. subtilis* and retaining more than 20% of the coenzyme binding activity of the wild type enzyme of *B. subtilis*;
   (b) contacting a sample suspected to contain an analyte with the reagent in the presence of a coenzyme, under conditions wherein the amount of the coenzyme bound to the glucose dehydrogenase variant to form a coenzyme glucose dehydrogenase variant complex is indicative of the amount of analyte to be determined; and
   (c) detecting the coenzyme glucose dehydrogenase variant complex.

2. The method of claim 1, wherein the glucose dehydrogenase variant has a threonine substitution at position 145 or a phenylalanine substitution at position 158 of the amino acid sequence of SEQ ID NO: 6.

3. The method of claim 2, wherein the glucose dehydrogenase variant has the amino acid sequence as shown in SEQ ID NO: 8 or SEQ ID NO: 10.

4. The method of claim 1, wherein the glucose dehydrogenase variant further comprises an amino acid segment capable of forming a metal chelate fused to said variant.

5. The method of claim 4, wherein the glucose dehydrogenase variant has the amino acid sequence as shown in SEQ ID NO: 14.

6. The method of claim 1, wherein the coenzyme is NAD(P)H.

7. The method of claim 1, wherein the coenzyme is formed by a reaction of an analyte with a precursor of the coenzyme, wherein the precursor is not capable of binding to the glucose dehydrogenase variant.

8. The method of claim 1, wherein the analyte is glucose.

9. The method of claim 1, wherein the sample is derived from a body fluid selected from serum, plasma, intestinal fluid or urine.

10. The method of claim 1, wherein the step of detecting the coenzyme glucose dehydrogenase variant complex is performed by measuring the fluorescence intensity.

11. The method of claim 1, wherein the reagent further comprising components for performing a liquid assay.

12. The method of claim 1, wherein the reagent further comprising components for performing a dry assay.

* * * * *